United States Patent [19]

Radüchel et al.

[11] Patent Number: 5,399,340
[45] Date of Patent: Mar. 21, 1995

[54] USE OF AMIDE COMPLEX COMPOUNDS

[75] Inventors: Bernd Radüchel; Heribert Schmitt-Willich; Heinz Gries; Gabriele Schuhmann-Giampieri; Hubert Vogler; Jürgen Conrad, all of Berlin, Germany

[73] Assignee: Schering Aktiengesellschaft, Berlin and Bergkamen, Germany

[21] Appl. No.: 49,400

[22] Filed: Apr. 20, 1993

Related U.S. Application Data

[63] Continuation of Ser. No. 725,808, Jul. 9, 1991, abandoned, which is a continuation-in-part of Ser. No. 569,132, Aug. 16, 1990, abandoned, which is a continuation-in-part of Ser. No. 494,803, Mar. 14, 1990, abandoned, which is a continuation of Ser. No. 100,681, Sep. 24, 1987, abandoned.

[30] Foreign Application Priority Data

Aug. 16, 1989 [DE] Germany .................. 39 27 444.6

[51] Int. Cl.⁶ ............................................. A61B 5/055
[52] U.S. Cl. ..................... 424/9; 128/653.4; 436/173; 436/806; 514/492; 514/502; 514/836
[58] Field of Search .............. 424/9; 436/173, 806; 128/653.4, 654; 514/184, 492, 502, 836; 534/16

[56] References Cited

U.S. PATENT DOCUMENTS

| | | | |
|---|---|---|---|
| 4,352,751 | 10/1982 | Wieder et al. | 260/112 R |
| 4,647,447 | 3/1987 | Gries et al. | 424/9 |
| 4,687,659 | 8/1987 | Quay | 424/9 |
| 4,714,607 | 12/1987 | Klaveness | 424/9 |
| 4,730,066 | 3/1988 | White | 556/50 |
| 4,746,507 | 5/1988 | Quag | 424/9 |
| 4,826,673 | 5/1989 | Dean et al. | 424/9 |
| 4,859,451 | 8/1989 | Quay et al. | 424/9 |
| 4,880,008 | 11/1989 | Lauffer | 128/654 |
| 4,899,755 | 2/1990 | Lauffer et al. | 128/654 |
| 4,909,257 | 3/1990 | Engelstad et al. | 128/654 |
| 4,980,148 | 12/1990 | Dean | 424/9 |
| 5,011,925 | 4/1991 | Rajogopalan et al. | 544/58.1 |
| 5,077,037 | 12/1991 | Wallace | 424/9 |
| 5,078,986 | 1/1992 | Bosworth et al. | 424/9 |
| 5,087,439 | 2/1992 | Quay | 424/9 |
| 5,087,440 | 2/1992 | Cacheris et al. | 424/9 |
| 5,098,692 | 3/1992 | Gries et al. | 424/9 |

FOREIGN PATENT DOCUMENTS

| | | |
|---|---|---|
| 78995/87 | 3/1988 | Australia . |
| 0299795 | 1/1989 | European Pat. Off. . |
| 1374979 | 11/1974 | United Kingdom . |
| 90/01024 | 2/1990 | WIPO . |
| 90/08138 | 7/1990 | WIPO . |

OTHER PUBLICATIONS

Lauterbur et al., Stereodynamics of Molecular Systems, Sarma (Ed.), Pergamon Press, Oxford, pp. 453–456 (1979).

*Primary Examiner*—Gary E. Hollinden
*Attorney, Agent, or Firm*—Millen, White, Zelano & Branigan

[57] ABSTRACT

Complex compounds of general Formula I $$Y-CH_2 \quad\quad\quad CH_2CO-N\begin{subarray}{l}R^3\\R^4\end{subarray}$$
$$\underset{XOOCCH_2}{\overset{|}{N}}-\underset{R^1}{\overset{|}{CH}}-(CH_2-N-CH_2)_n-\underset{R^2}{\overset{|}{CH}}-\underset{CH_2COOX}{\overset{|}{N}}$$

wherein

X is a hydrogen atom and/or a metal ion equivalent of at least one element of atomic numbers 21–29, 42, 44 or 58–70, with at least two of the substituents X representing a metal ion equivalent, and $R^1$, $R^2$, $R^3$, $R^4$, Y and n are defined herein, as well as their salts with organic and/or inorganic bases, are valuable compounds for organ-specific NMR diagnostics.

27 Claims, No Drawings

USE OF AMIDE COMPLEX COMPOUNDS

CROSS-REFERENCE TO RELATED APPLICATIONS

This application is a continuation of Ser. No. 07/725,808, filed Jul. 9, 1991, abandoned, which is a continuation-in-part of Ser. No. 07/569,132, filed Aug. 16, 1990, abandoned, which is a continuation-in-part of Ser. No. 07/494,803, filed Mar. 14, 1990, abandoned, which is a continuation of Ser. No. 07/100,681, filed Sep. 24, 1987, (abandoned), all of which are entirely incorporated by reference herein.

In addition, this application is related to U.S. application Ser. Nos. 07/078,507 (filed Jul. 28, 1987), 07/063,355 (filed Jun. 18, 1987), 07/020,301 (filed Mar. 2, 1987), 07/020,300 (filed Mar. 2, 1987), 07/020,993 (filed Mar. 2, 1987), 07/020,992 (filed Mar. 2, 1987), 06/936,055 (filed Nov. 28, 1986), 06/876,497 (filed Jun. 20, 1986), and 06/627,143 (filed Jul. 2, 1984), each of which is a divisional, continuation or continuation-in-part of Ser. No. 06/573,184 (filed Jan. 23, 1984), now U.S. Pat. No. 4,647,447, which is a continuation-in-part of Ser. No. 06/401,594 (filed Jul. 26, 1982), and this application is a continuation-in-part of all said applications directly or indirectly and all of which applications are entirely incorporated by reference herein.

SUMMARY OF THE INVENTION

This invention relates to physiologically compatible amide complex compounds and the use thereof in the production of agents for organ-specific NMR diagnostics and for cases involving patients with renal insufficiency, as well as NMR methods utilizing these compounds.

European Patent Publication Number 263,059 claims compounds of Formula I

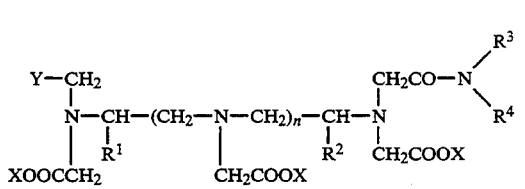

(I)

wherein n is 0, 1 or 2, $R^1$ and $R^2$ independently are hydrogen atoms, lower alkyl groups, phenyl groups, benzyl groups or, if n is 0, jointly can also form a trimethylene or a tetramethylene group, $R^3$ is a saturated, unsaturated, straight-chain or branched-chain or cyclic hydrocarbon residue of up to 16 carbon atoms or, if $R^4$ is a hydrogen atom, at least one $R^3$ is a cycloalkyl group, or an aryl or aralkyl group optionally substituted by one or several di-$C_1$-$C_6$-alkylamino groups or by one or several $C_1$-$C_6$-alkoxy groups, $R^4$ is a hydrogen atom, or a saturated, unsaturated, straight-chain or branched-chain or cyclic hydrocarbon residue of up to 16 carbon atoms, or $R^3$ and $R^4$ jointly form a saturated or unsaturated 5- or 6-membered ring which is optionally substituted by one or several of $C_1$-$C_6$-alkyl, $C_1$-$C_5$-hydroxyalkyl, optionally hydroxylated or $C_1$-$C_6$-alkoxylated $C_2$-$C_6$-acyl, hydroxy, carbamoyl, carbamoylsubstituted $C_1$-$C_6$-alkyl residue, carbamoyl substituted on the carbamoyl nitrogen by one or two $C_1$-$C_6$-alkyl residue(s)—which can also form a ring optionally containing an oxygen atom—or $C_1$-$C_6$-acylamino or $C_1$-$C_6$-alkyl-amino; this 5- or 6-membered ring optionally containing a further nitrogen, oxygen or sulfur atom, or carbonyl group, X means a hydrogen atom and/or a metal ion equivalent, Y is a COOX or

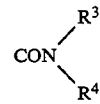

group, as well as their salts with organic and/or inorganic bases.

Compounds having the anion of one of these complex-forming amides and one or several central ions of an element of atomic numbers 21-29, 31, 32, 38, 39, 42-44, 49, 57-83 and optionally one or several cations of an inorganic and/or organic base or amino acid are suited for the production of NMR, X-ray and radiology diagnostic media.

It has now been found that surprisingly an unexpected pharmacokinetic behavior is displayed by compounds of this general Formula I if these compounds contain at least one element of atomic numbers 21-29, 42, 44 or 58-70, i.e., at least two of the substituents X must stand for a metal ion equivalent of these elements, but in particular compounds of general Formula I wherein N is the number 1, $R^1$ and $R^2$ are hydrogen atoms, $R^3$ is a saturated, unsaturated, straight-chain or branched-chain or cyclic hydrocarbon residue of up to 16 carbon atoms or, if $R^4$ is a hydrogen atom, at least one $R^3$ is a cycloalkyl group, or an aryl or aralkyl group optionally substituted by one or several di-$C_1$-$C_6$-alkylamino groups or by one or several $C_1$-$C_6$-alkoxy groups, $R^4$ is a hydrogen atom or a saturated, unsaturated, straight-chain, branched-chain or cyclic hydrocarbon residue of up to 16 carbon atoms, X is a hydrogen atom and/or a metal ion equivalent of at least one element of atomic numbers 21-29, 42, 44 or 58-70, Y is a COOX or

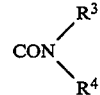

group, with the proviso that at least two of the substituents X stand for a metal ion equivalent, as well as their salts with organic and/or inorganic bases.

Thus, for example, MAGNEVIST®, thus far the only NMR contrast medium permitted worldwide, is distributed upon intravenous injection in an extra-cellular fashion and is excreted via the kidneys by glomerular secretion. Passage of intact cell membranes and extrarenal excretion are practically not at all observed.

MAGNEVIST ® is especially well suited for the diagnosis of pathological regions (for example, inflammations, tumors, infarctions, etc.).

Contrast media exhibiting an at least partial extrarenal excretion would be desirable, especially for patients with limited kidney function (renal insufficiency) where MAGNEVIST ® is excreted only very slowly and, in part, can be removed from the organism only with the aid of a dialysis device.

Consequently, there is a need for NMR contrast media exhibiting a different pharmacokinetic behavior and thus higher organ specificity than MAGNEVIST ®.

Accordingly, it is an object of this invention to provide such compounds and media and methods of using same.

Upon further study of the specification and appended claims, further objects and advantages of this invention will become apparent to those skilled in the art.

It has been found that the above-mentioned compounds surprisingly show the desired property: renal elimination as well as excretion with the feces.

Surprisingly, elimination via the gallbladder, however, is not the only extrarenal path of elimination: in NMR studies on rats, upon intravenous administration of the compounds of this invention, a contrast enhancement of the gastrointestinal tract has also been unexpectedly observed. The kidneys, as well as implanted tumors, are likewise visualized with improved contrast.

Elimination (secretion) by way of the stomach has the advantage that contrasting of abdominal structures (e.g., pancreas) from the gastrointestinal tract is made possible, with a simultaneous contrast enhancement of pathological processes (tumors, inflammations). Imaging of the renal system, of the liver and gallbladder, and the bile ducts can moreover likewise be achieved. Besides the improved visualization of ulcers and stomach carcinomas, it is also possible to perform studies on gastric acid secretion with the aid of imaging procedures.

Accordingly, by making the compounds of this invention available, help can be extended to patients with renal insufficiency as well as patients suffering from gastrointestinal disorders (at least 10% of the population in the Western industrial countries). Most of these patients, as well as a large number of patients suspected of harboring such disease, must submit to diagnostic tests. At present, two methods suitable for this purpose are utilized above all: endoscopy and X-ray diagnostics with the aid of barium contrast media.

These tests exhibit various drawbacks: they carry the risk of radiation stress, cause trauma, are connected with inconveniences, occasionally even with risks for the patient, and thus can evoke psychological stress. In most cases, these tests must be repeated; their performance is relatively complicated, require the patient's active cooperation (e.g., assumption of a specific bodily attitude) and frequently cannot be employed in case of frail and high-risk patients.

The object of providing novel diagnostic methods for the identification and localization of gastrointestinal diseases, which methods do not exhibit these drawbacks, has thus likewise been attained by the complex compounds and agents as mentioned above.

Their pharmacokinetics permit, even without specific measures, an improvement in the diagnosis of numerous diseases. The complexes for the most part are excreted again in unchanged form and rapidly so that, especially also in case of using relatively toxic metallic ions, no damaging effects are observed even at high dosage.

The practical use of the novel complexes is also facilitated by their favorable chemical stability.

Compounds of formula I, wherein X is hydrogen, are called "complexing agents", and those wherein at least two of the substituents X are a metal ion equivalent are called "metal complexes".

For use in NMR diagnostics, the central ion of the complex salt will be paramagnetic. These are, in particular, the divalent and trivalent ions of the elements of atomic numbers 21–29, 42, 44 and 58–70. Suitable ions include, for example, the chromium(III), manganese(II), iron(II), cobalt(II), nickel(II), copper(II), praseodymium(III), neodymium(III), samarium(III) and ytterbium(III) ions. On account of their very strong magnetic moment, the gadolinium(III), terbium(III), dysprosium(III), holmium(III), erbium(III) and iron(III) ions are especially preferred.

Suitable alkyl substituents $R^1$ and $R^2$ are hydrocarbons of 1–8, preferably 1–4 carbon atoms, such as, for example, methyl, ethyl, propyl, isopropyl, n-, sec- or tert.-butyl, isobutyl, and all isomers of pentyl, hexyl, heptyl and octyl.

Suitable substituents $R^3$ and $R^4$ are saturated (e.g., alkyl), unsaturated (e.g., alkenyl), straight-chain or branched-chain or cyclic hydrocarbons of up to 16 carbon atoms, preferably 1–10 C atoms, most preferably saturated hydrocarbons of 1–10 carbon atoms, especially saturated hydrocarbons of 1–5 carbon atoms. Examples include methyl, ethyl, propyl, isopropyl, butyl, isobutyl, pentyl, cyclopentyl, cyclohexyl, propenyl, etc.

Other suitable groups are the other alkyl groups mentioned above for $R^1$ and $R^2$ and isomers containing 9–16 C atoms as well as their alkenyl counterparts.

When $R^4$ is a hydrogen atom, at least one $R^3$ is preferably $C_6$–$C_{10}$-aryl or $C_6$–$C_{10}$-Ar-$C_1$–$C_6$-alkyl group, e.g., phenyl or benzyl group, optionally substituted by one or several (e.g., up to three) di-$C_1$- to $C_6$-alkylamino groups or by one or several (e.g., up to three) $C_1$- to $C_6$-alkoxy groups.

In addition, when $R^4$ is a hydrogen atom, $R^3$ can also preferably be a cycloalkyl group, as mentioned above. The cycloalkyl group generally contains 3–16 carbon atoms, preferably 4–7 carbon atoms.

The heterocyclic 5- or 6-membered ring formed by $R^3$ and $R^4$ with inclusion of the amide nitrogen can be saturated, unsaturated and/or substituted and can optionally contain a nitrogen, oxygen or sulfur atom or carbonyl group.

The heterocycle can be substituted by hydroxy, $C_1$–$C_6$-alkyl, e.g., methyl, ethyl, propyl, isopropyl, butyl, $C_1$–$C_5$-hydroxyalkyl, e.g., hydroxymethyl, hydroxyethyl, or by $C_2$–$C_6$-acyl (e.g., alkanoyl), for example acetyl, propionyl, which can, if desired, be substituted by hydroxy or $C_1$–$C_6$-alkoxy, e.g., methoxy, ethoxy, etc.

A further substituent that can be mentioned is carbamoyl, linked to the heterocycle directly or separated by a $C_1$–$C_6$-alkylene group, for example methylene, ethylene, propylene, and which can also be substituted at the nitrogen, if desired, by one or two $C_1$–$C_6$-alkyl residue(s), e.g., methyl, ethyl, propyl, isopropyl, etc. The alkyl groups can, optionally, form a ring, such as, for example, a pyrrolidine or piperidine ring. The carbamoyl nitrogen can also be part of a morpholine ring, i.e., the latter ring can have an O atom.

Another possible substituent on the heterocycle that can be mentioned is an optionally $C_1$–$C_6$-alkylated or $C_1$–$C_6$-acylated (e.g., alkanoylated) primary or secondary amino group, such as, for example, the methyl-, ethyl-, acetyl-, propionyl-, amino-, etc., group.

If the heterocycle is substituted, the total number of substituents is 1 to 3.

Suitable heterocycles are, for example: the pyrrolidinyl, piperidyl, pyrazolidinyl, pyrrolinyl, pyrazolinyl, piperazinyl, morpholinyl, imidazolidinyl, oxazolidinyl, thiazolidinyl rings.

If not all of the acidic hydrogen atoms are substituted by the central ion, then one, several, or all remaining hydrogen atom(s) can be replaced by cations of inorganic and/or organic bases or amino acids. Suitable inorganic cations include, for example, the lithium ion, the potassium ion, the calcium ion and, in particular, the sodium ion. Suitable cations of organic bases include, inter alia, those of primary, secondary or tertiary amines, e.g., ethanolamine, diethanolamine, morpholine, glucamine, N,N-dimethylglucamine and especially N-methylglucamine. Suitable cations of amino acids include, for example, those of lysine, of arginine, and of ornithine.

Introduction of amide groups for the production of the complexing agents, i.e., of compounds of general Formula I wherein X means hydrogen, takes place by conventional partial conversion of activated carboxyl groups into amide groups of the respectively suited tetra-, penta- and hexacarboxylic acids—in correspondence with the desired final product. All of the synthesis pathways known to a person skilled in the art are suitable for this procedure.

One example is the reaction of the anhydrides or esters of general Formulae II, IV, V and VI:

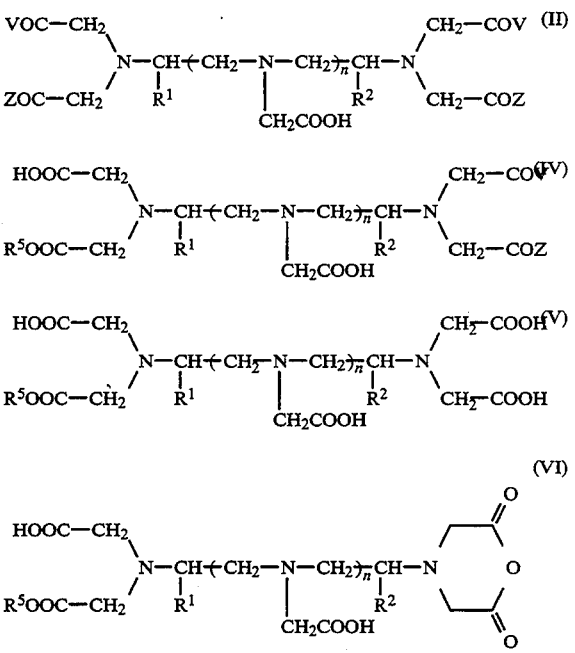

wherein $R^1$, $R^2$ and n have the above-mentioned meanings, V and Z jointly mean an oxygen atom, or V is a hydroxy group and Z is tile grouping $OR^5$, wherein $R^5$ is a $C_1$–$C_6$-alkyl residue, with amines of general Formula III

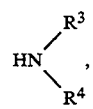

wherein $R^3$ and $R^4$ have the meanings given above.

Examples of suitable amines include: dimethylamine, diethylamine, di-n-propylamine, diisopropylamine, di-n-butylamine, diisobutylamine, di-sec-butylamine, N-methyl-n-propylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, 4-methoxybenzylamine, morpholine, pyrrolidine, piperidine, N-methylpiperazine, N-ethylpiperazine, N-(2-hydroxyethyl)piperazine, N-(hydroxymethyl)piperazine, piperazinoacetic acid isopropylamide, N-(piperazinomethylcarbonyl)morpholine, N-(piperazinomethylcarbonyl)pyrrolidine, 2-(2-hydroxymethyl)piperidine, 4-(2-hydroxyethyl)piperidine, 2-hydroxymethylpiperidine, 4-hydroxymethylpiperidine, 2-hydroxymethylpyrrolidine, 3-hydroxypiperidine, 4-hydroxypiperidine, 3-hydroxypyrrolidine, 4-piperidone, 3-pyrroline, piperidine-3-carboxylic acid amide, piperidine-4-carboxylic acid amide, piperidine-3-carboxylic acid diethylamide, piperidine-4-carboxylic acid dimethylamide, 2,6-dimethylpiperidine, 2,6-dimethylmorpholine, N-acetylpiperazine, N-(2-hydroxypropionyl)piperazine, N-(3-hydroxypropionyl)piperazine, N-(methoxyacetyl)piperazine, 4-(N-acetyl-N-methylamino)piperidine, piperidine-4-carboxylic acid (3-oxapentamethylene)amide, piperidine-3-carboxylic acid (3-oxapentamethylene)amide, N-(N',N'-dimethylcarbamoyl)piperazine, pyrazoline, pyrazolidine, imidazoline, oxazolidine, thiazolidine, etc.

The saponification of any ester groups that may still be present takes place according to methods known to one skilled in the art, for example, by alkaline hydrolysis.

The acid anhydrides of general Formula II can be prepared conventionally, for example in accordance with the mode of operation disclosed in U.S. Pat. Nos 3,660,388 or DOS 1,695,050, with acetic anhydride in pyridine. However, in certain instances, it is especially advantageous to conduct the step of splitting off water in a gentle fashion with carbodiimides in a suitable solvent, such as, for example dimethylformamide or dimethylacetamide.

The preparation of the monoanhydrides of general Formula VI will be described by using as the example the monoanhydride of diethylenetriaminepentaacetic acid ethyl ester starting with the monoethyl ester of DTPA (J. Pharm. Sci. 68: 194, 1979):

$N^3$-(2,6-Dioxomorpholinoethyl)-$N^6$-(ethoxycarbonylmethyl)-3,6-diazaoctanedioic Acid A suspension of 21.1 g (50 millimoles) of $N^3$,$N^6$-bis(-carboxymethyl)-$N^9$-(ethoxycarbonylmethyl)-3,6,9-triazaundecanedioic acid in 250 ml of acetic anhydride is agitated for 3 days at room temperature after adding 42.2 ml of pyridine. Then the precipitate is suctioned off, washed three times with respectively 50 ml of acetic anhydride and subsequently stirred for several hours with absolute diethyl ether. After suctioning off the product, washing same with absolute diethyl ether and drying under vacuum at 40° C., 18.0 g (=89% of theory) of a white powder is obtained, mp 195°–196° C.

Analysis (based on anhydrous substance): Calculated: C 47.64 H 6.25 N 10.42 Found: C 47.54 H 6.30 N 10.22

The reaction of the acid anhydrides to the amides can be performed in the liquid phase. Suitable reaction media include, for example, water, dipolar aprotic solvents, such as acetonitrile, N-methylpyrrolidone, dimethylformamide, dimethylacetamide, and the like, or mixtures thereof. The reaction temperatures range between about 0° C. and 100° C., temperatures of 20°-80° C. being preferred. The reaction periods range between 0.5 hour and 2 days, preferably between 1 hour and 36 hours.

The esters of general Formula V are produced conventionally, for example according to the processes described in R. A. Guilmette et al., J. Pharm. Sci. 68: 194 (1979).

Aminolysis of the esters takes place in the liquid phase, for example in a suitable higher-boiling solvent, such as dimethylformamide, dimethylacetamide or dimethyl sulfoxide. The reaction temperatures are around 20° C. to 200° C., temperatures of 100°-180° C. being preferred. The reaction times range between 2 hours and 2 days, reaction periods of between 4 hours and 36 hours being the preferred ones.

Moreover, all methods known to a person skilled in the art for converting carboxyl groups into amide groups can be employed for the synthesis of the complexing agents of Formula I according to this invention, for example, the method by Krejcarek and Tucker, Biochm. Biophys. Res. Commun. 77: 581 (1977) via mixed anhydrides.

The resultant compounds of Formula I wherein X is a hydrogen atom represent complex-forming media. They can be isolated and purified, or they can be converted without isolation into metal complexes of general Formula I wherein at least two of the substituent X mean a metal ion equivalent.

The metal complexes are prepared conventionally by the methods disclosed in Patents EP 71564, EP 130934 and DOS 3,401,052, by dissolving or suspending the metal oxide or a metal salt (e.g., the nitrate, acetate, carbonate, chloride or sulfate) of the element of atomic numbers 21-29, 42, 44 or 58-70 in water and/or a lower alcohol (such as methanol, ethanol or isopropanol) and reacting with a solution or suspension of the equivalent amount of the complex-forming acid of Formula I wherein X means a hydrogen atom and subsequently, if desired, substituting any acidic hydrogen atoms of acid groups present by cations of inorganic and/or organic bases or amino acids.

Neutralization is herein effected with the air of inorganic bases (for example, hydroxides, carbonates or bicarbonates) of, for example, sodium potassium, lithium and/or organic bases such as, inter alia, primary, secondary and tertiary amines, such as, for example, ethanolamine, morpholine, glucamine, N-methyl- and N,N-dimethylglucamine, as well as basic amino acids, such as, for example, lysine, arginine and ornithine.

In order to prepare the neutral complex compounds, it is possible, for example, to add to the acidic complex salts in an aqueous solution or suspension such an amount of the desired bases that the neutral point is reached. The resultant solution can subsequently be evaporated to dryness under vacuum. It is frequently advantageous to precipitate the thusformed neutral salts by adding water-miscible solvents, such as, for example, lower alcohols (methanol, ethanol, isopropanol, etc.), lower ketones (acetone etc.), polar ethers (tetrahydrofuran, dioxane, 1,2-dimethoxyethane, etc.), and to obtain in this way crystallized products which can be readily isolated and easily purified. It has proven to be especially advantageous to add the desired base to the reaction mixture as early as during the complexing reaction, thereby saving a process step.

If the acidic complex compounds contain several free acidic groups, then it is frequently expedient to prepare neutral mixed salts containing inorganic as well as organic cations as the counterions.

This can be done, for example, by reacting the complexing acid in an aqueous suspension or solution with the oxide or salt of the element yielding the central ion and with half the amount of an organic base needed for neutralization, isolating the thusformed complex salt, purifying same if desired, and then combining same for complete neutralization with the required amount of inorganic base. The sequence of adding the bases can also be reversed.

The diagnostic media are likewise produced in a manner known per se by suspending or dissolving the complex compounds of this invention—optionally after adding the additives customary in galenic pharmacy—in an aqueous medium and subsequently sterilizing the suspension or solution, if desired. Suitable additives are, for example, physiologically acceptable buffers (such as, e.g., tromethamine), small additions of complexing agents (such as, e.g., diethylenetriaminepentaacetic acid) or, if necessary, electrolytes such as, for example, sodium chloride or, if needed antioxidants, such as ascorbic acid, for example.

If, for enteral administration or other purposes, suspensions or solutions of the media of this invention in water or a physiological saline solution are desirable, they can be mixed with one or several auxiliary agents customary in galenic pharmacy (for example methylcellulose, lactose, mannitol) and/or tensides (e.g., lecithins, TWEENS ®, MYRJ ®) and/or flavoring substances for taste improvement (e.g. ethereal oils).

In principle, it is also possible to prepare the diagnostic media of this invention even without isolation of the complex salts. In any event, special care must be directed toward effecting the chelate formation so that the salts and salt solutions according to this invention are practically devoid of toxically active metal ions that are not complexed.

This can be ensured, for example, with the aid of color indicators, such as xylenol orange, by control titrations during the manufacturing process. Consequently, the invention also relates to processes for preparing the complex compounds and their salts. The final safety feature resides in purification of the isolated complex salt.

For nuclear spin tomography diagnostics in accordance with this invention, the diagnostic media are administered in a dosage of 1 $\mu$mol/kg to 5 mmol/kg, preferably 10 $\mu$mol to 0.5 mmol/kg of the complex salt according to the invention. In case of intravenous injection, aqueous formulations are used with a concentration of 50 $\mu$mol/l to 2 mol/l, preferably 100 mmol/l to 1 mol/l. Rectal as well as oral administration is preferably performed with solutions of a concentration of 0.1 mmol to 100 mmol/l. The volumes administered range from about 5 ml to 2 l, in dependence on the diagnostic problem. Thus, the diagnostic media are intended for enteral and parenteral administration to mammals, including humans.

The diagnostic media fulfill the variegated requirements for suitability as contrast media for nuclear spin tomography. Thus, they are excellently suited, upon oral or parenteral administration, for improving the information content of the image obtained with the aid of the nuclear spin tomograph, by increasing the signal intensity. They show furthermore the high efficacy necessary for burdening the body with minimal amounts of foreign substances, and the good compatibility required for maintaining the noninvasive character of the tests.

The high water solubility of the diagnostic media permits production of highly concentrated solutions so that the volume load on the circulation is maintained within tolerable limits and dilution by body fluids is compensated, i.e., NMR diagnostic agents must show 100 to 1000 times the water solubility of that for in vitro NMR spectroscopy. Furthermore, the agents of this invention display not only high stability so that release or exchange of the—toxic per se—ions not covalently bound to the complexes takes place only extremely gradually within the time wherein the contrast media are again entirely eliminated.

The agents of this invention can also be utilized for radiation therapy. Thus, complexes of gadolinium are excellently suited for neutron capture therapy due to the large capture cross section. If the medium of this invention is intended for use in the version of radiation therapy proposed by R. L. Mills et al. [Nature 336: 787 (1988)], then the central ion must be derived from a Mössbauer isotope, such as, for example, $^{57}$Fe or $^{151}$Eu.

In their administration, the agents of this invention can also be given together with a suitable vehicle, such as, for example, serum or physiological saline solution and/or together with a protein, such as, for example, human serum albumin. The dosage herein is dependent on the type of cellular disorder and on the properties of the metal complex utilized.

Consequently, the objective has been achieved overall of opening up novel possibilities in diagnostic medicine by means of the recited complex compounds.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 39 27 444.6, filed Aug. 16, 1989, are hereby incorporated by reference.

EXAMPLE 1

(a) 6-Carboxymethyl-3-ethoxycarbonylmethyl-9-phenylaminocarbonylmethyl-3,6,9-triazaundecanedioic Acid At 0° C., 2.42 g (6 mmol) of $N^3$-(2,6-dioxomorpholinoethyl)-$N^6$-(ethoxycarbonylmethyl)-3,6-diazaoctanedioic acid is combined in DMF with 4.16 ml (3.04 g, 30 mmol) of triethylamine and 559 mg (6 mmol) of aniline and stirred overnight at room temperature. Then the clear solution is concentrated under vacuum and the residue chromatographed on silica gel with dichloromethane/methanol/acetic acid/water (5:3:1:1) as the mobile phase. The combined fractions are passed over approximately 10 ml of "Amberlite" IR 120 (H+ form) and the acidic eluate is concentrated.

Yield: 2.35 g (79%) Calculated: C 53.21 H 6.50 N 11.29 Found: C 53.01 H 6.55 N 11.26

(b) 3,6,9-Tris(carboxymethyl)-3,6,9-triazaundecanedioic Acid Phenyl Monoamide 1.5 g (3 mmol) of the ethyl ester described in Example 1(a) is dissolved in 2N NaOH and stirred for 2 hours at room temperature. A pH of 7 is set by adding "Amberlite" IR 120 (H+ form), the mixture is filtered off, and the neutral solution is passed over about 16 ml of "Amberlite" IR 120 (H+). The acidic eluate is concentrated and additionally dried under vacuum at 50° C.

Yield: 1.3 g (92.5%) Calculated: C 51.27 H 6.03 N 11.96 Found: C 51.19 H 5.99 N 11.91

(c) Gadolinium Complex of 3,6,9-Tris (carboxymethyl)-3,6,9-triazaundecanedioic Acid Phenyl Monoamide 936 mg (2 mmol) of the complexing acid obtained according to Example 1(b) is dissolved in about 40 ml of water and combined at 80° C. with 362 mg (1 mmol) of $Gd_2O_3$. After 30 minutes, the almost clear solution is filtered off and the filtrate is freeze-dried.

Yield: 1.23 g (98.8%), based on anhydrous substance. Calculated: C 38.57 H 4.05 N 9.00 Gd 25.25 Found: C 38.33 H 4.10 N 9.03 Gd 24.99

EXAMPLE 2

Preparation of a Solution of the N-Methylglucamine Salt of the Gadolinium Complex of 3,6,9-Tris(carboxymethyl)-3,6,9-triazaundecanedioic Acid Phenyl Monoamide 1.87 g (3 mmol) of the gadolinium complex of 3,6,9-tris (carboxymethyl)-3,6,9-triazaundecanedioic acid phenyl monoamide (Example 1) is suspended in 5 ml of water pro injectione and combined with 0.586 g (3 mmol) of N-methylglucamine, thus dissolving the complex. The mixture is filled up with water to 10 ml, the solution is introduced into a vial and subjected to heat sterilization.

$T_1$ relaxation (1/mmol sec) is:
in water: 3.79±0.16
in plasma: 5.45±0.68

EXAMPLE 3

Preparation of a Solution of the Sodium Salt of the Gadolinium(III) Complex of 3,6,9-Tris(carboxymethyl)-3,6,9-triazaundecanedioic Acid Phenyl Monoamide 62.27 g (0.1 mol) of the gadolinium complex obtained according to Example 1(c) is suspended in 800 ml of water pro injectione (p.i.) and dissolved at pH 7.2 by dropwise addition of normal sodium hydroxide solution. After adding 0.2 g of tromethamine, the mixture is filled up with water p.i. to 1000 ml, the solution is dispensed into bottles and heat-sterilized.

EXAMPLE 4

(a) 3,6,9-Tris(carboxymethyl)-3,6,9-triazaundecanedioic Acid (N,N'-Diphenyl)diamide 42.88 g (120 mmol) of DTPA bis-anhydride is suspended in 330 ml of dimethylformamde and cooled in an ice bath under agitation to about 5° C. Within 50 minutes, a solution of 32.9 ml (360 mmol) of aniline in 30 ml of dimethylformamide is added dropwise. The mixture is stirred for another hour in an ice bath, then overnight at room temperature. After this time, a slightly turbid solution has formed. The solvent is removed under vacuum, and the smeary residue is triturated with diethyl ether to remove traces of solvent. The residue is combined with 500 ml of water and dissolved by adding 20 ml of 11N sodium hydroxide solution. The solution is combined with 3.5 g of active carbon, filtered, and freeze-dried, thus obtaining 73.9 g of the sodium salt of the title compound as a powder.

(b) Gadolinium Complex of 3,6,9-Tris(carboxymethyl)-3,6,9-triazaundecanedioic Acid (N,N'-Diphenyl)diamide 10.9 g of gadolinium oxide (30 mmol) is heated under reflux with 10.6 ml of glacial acetic acid and 150 ml of water for 20 minutes. The solution is filtered through a 0.1 μm membrane filter, combined with 35.3 g (60 mmol) of the ligand obtained according to 4(a), and heated for 90 minutes to 80° C. The solution is stirred with 2.1 g of active carbon for 30 minutes, filtered, and then passed in succession over an anion exchange column (200 ml IRA-410) and 100 ml of cation exchanger (IRC-50). The eluates from the columns a filtered through a 0.1 μm membrane filter and freeze-dried, thus obtaining 17.6 g of the title compound as a white powder.

Analysis: Calculated: C 44.75 H 4.33 Gd 22.54 N 10.04 Found: C 44.60 H 4.44 Gd 22.42 N 9.89

EXAMPLE 5

(a) 3,6,9-Tris (carboxymethyl)-3,6,9-triazaundecanedioic Acid (N,N'-Dibenzyl)diamide 42.88 g (120 mmol) of DTPA bis-anhydride is suspended in 330 ml of dimethylformamide and cooled in an ice bath under agitation to 5° C. Within one hour, a solution of 39.3 ml (360 mmol) of benzylamine in 30 ml of dimethylformamide is added dropwise. The mixture is stirred for another hour in the ice bath, then overnight at room temperature. After removal of the solvent under vacuum, the residue is triturated with diethyl ether, combined with 500 ml of water, and dissolved by adding 20 ml of 11N sodium hydroxide solution. After freeze-drying, 71 g of the sodium salt of the title compound is obtained as a light-yellow powder.

(b) Gadolinium Complex of 3,6,9-Tris (carboxymethyl)-3,6,9-triazaundecanedioic Acid (N,N'-Dibenzyl)diamide 10.9 g of gadolinium oxide (30 mmol) is heated under reflux with 10.6 ml of glacial acetic acid and 150 ml of water for 20 minutes. The solution is filtered over a 0.1 μm membrane filter, combined with 37 g (60 mmol) of the ligand obtained according to 5(a), and heated for 90 minutes to 80° C. The solution is stirred with 3 g of active carbon for 30 minutes, filtered,- and then passed in succession over an anion exchange column (200 ml IRA-410) and 100 ml cation exchange column (100 ml IRC-50). The eluates are filtered through a 0.1 μm membrane filter and freeze-dried, thus obtaining 18 g of the title compound as a white powder.

Analysis: Calculated: C 46.33 H 4.72 Gd 21.66 N 9.65 Found: C 46.46 H 4.49 Gd 21.50 N 9.81

EXAMPLE 6

(a) 6-Carboxymethyl-3-ethoxycarbonylmethyl-9-benzylaminocarbonylmethyl-3,6,9-triazaundecanedioic Acid 5.04 g (12.5 mmol) of $N^3$-(2,6-dioxomorpholinoethyl)-$N^6$-(ethoxycarbonylmethyl)-3,6-diazaoctanedioic acid is suspended in 65 ml of dimethylformamide, stirred in an ice bath and combined, in succession, with 8.7 ml (62.5 mmol) of triethylamine and 1.34 g (12.5 mmol) of benzylamine. The mixture is then stirred for another 2 hours in the ice bath, then overnight at room temperature. The solvent is removed by vacuum distillation, the residue is agitated with diisopropyl ether, suctioned off, and dried. For further purification, the residue is dissolved in such a quantity of 11N sodium hydroxide solution that a pH of 7 is just attained. To this mixture is added 5 g of silica gel, the suspension is dried under vacuum, and the residue is introduced into a column of 350 g of silica gel charged with a mixture of chloroform/methanol/glacial acetic acid/water (1750/1050/350/350). The product is eluted with the same solvent and, after evaporation of the solvent, 4.98 g of a colorless, smeary substance is obtained which is dissolved in 35 ml of water and passed over a column with 35 ml of the cation exchanger "IR 120". The column is washed with 70 ml of water, the combined eluates are evaporated under vacuum, and the residue is triturated with diethyl ether, thus obtaining 2.65 g of the title compound as a white powder.

Analysis: Calculated: C 54.11 H 6.71 N 10.97 Found: C 53.95 H 6.88 N 11.23

(b) 3,6,9-Tris(carboxymethyl)-3,6,9-triazaundecanedioic Acid Benzyl Monoamide

A solution of 2.26 g of the compound prepared according to Example 6(a) in 46 ml of 1N sodium hydroxide solution is allowed to stand for 2.5 hours at room temperature, and the solution is then passed over a column of 110 ml of cation exchanger "IR 120". Elution is first carried out with 200 ml of water, and this fraction is discarded. Then, 600 ml of 0.5N ammonia is used for elution; this eluate is adjusted to pH 2.3 by adding "IR 120", and the solution is subjected to freeze-drying, thus obtaining 1.50 g of the title compound as a white powder.

Analysis: Calculated: C 52.28 H 6.27 N 11.61 Found: C 52.44 H 6.32 N 11.80

(c) Gadolinium Complex of 3,6,9-Tris(carboxymethyl)-3,6,9-triazaundecanedioic Acid Benzyl Monoamide 965 mg (2 mmol) of the compound produced in accordance with Example 6(b) is heated with 40 ml of water and 362 mg (1 mmol) of gadolinium oxide for one hour to 80° C. The mixture is cooled to room temperature, the solution is filtered through a 0.1 μm membrane filter, and the compound is isolated by freeze-drying, yielding 1.15 g of the title compound as a white powder.

Analysis: Calculated: C 39.61 H 4.27 Gd 24.70 N 8.80 Found: C 39.50 H 4.48 Gd 24.61 N 8.97

EXAMPLE 7

Dysprosium(III) Complex of 3,6,9-Tris (carboxymethyl)-3,6,9-triazaundecanedioic Acid Benzyl Monoamide 965 mg (2 mmol) of 3,6,9-tris(carboxymethyl)-3,6,9-triazaundecanedioic acid benzyl monoamide (Example 6b) is heated with 40 ml of water and 373 mg (1 mmol) of dysprosium(III) oxide for one hour to 80° C. The mixture is cooled to room temperature, the solution is filtered through a 0.1 μm membrane filter, and the compound is isolated by freeze-drying, thus obtaining 1.22 g of the title compound as a white powder.

Analysis: Calculated: C 39.29 H 4.24 Dy 25.31 N 8.73 Found: C 39.41 H 4.51 Dy 25.19 N 8.70

EXAMPLE 8

(a) 6-Carboxymethyl-3-ethoxycarbonylmethyl-9-tert-butylaminocarbonylmethyl-3,6,9-triazaundecanedioic Acid At 0° C., 2.42 g (6 mmol) of $N^3$-(2,6-dioxomorpholinoethyl)-$N^6$-(ethoxycarbonylmethyl)-3,6-diazaoctanedioic acid is combined in DMF with 4.16 ml (3.04 g, 30 mmol) of triethylamine and 0.64 g (6 mmol) of tert-butylamine and stirred overnight at room temperature. The clear solution is then concentrated under vacuum and the residue chromatographed on silica gel with dichloromethane/methanol/acetic acid/water (5:3:1:1) as eluent. The combined fractions are passed over about 10 ml of "Amberlite" IR 120 (H+ form), and the acidic eluate is concentrated.

Yield: 2.14 g (75%) Calculated: C 50.41 H 7.62 N 11.76 Found: C 50.26 H 7.66 N 11.80

(b) 3,6,9-Tris(Carboxymethyl)-3,6,9-triazaundecanedioic Acid tert-Butyl Monoamide 1.43 g (3 mmol) of the ethyl ester described in Example 8(a) is dissolved in 2N NaOH and stirred for 2 hours at room temperature. By addition of "Amberlite" 120 (H+ form), the mixture is adjusted to pH 7, filtered off, and the neutral solution passed over about 16 ml of "Amberlite" IR 120 (H+). The acidic eluate is concentrated and further dried at 50° C. under vacuum. Yield: 1.20 g (89%).

Calculated: C 48.21 H 7.19 N 12.49 Found: C 48.13 H 7.24 N 12.41

(c) Gadolinium Complex of 3,6,9-Tris (carboxymethyl)-3,6,9-triazaundecanedioic Acid tert-Butyl Monoamide 897 mg (2 mmol) of the complex-forming acid obtained according to Example 8(b) is dissolved in about 40 ml of water and combined at 80° C. with 362 mg (1 mmol) of $Gd_2O_3$. After 30 minutes, the almost clear solution is filtered and the filtrate freeze-dried.

Yield: 1.19 g (99%), based on anhydrous substance. Calculated: C 35.87 H 4.85 N 9.30 Gd 26.09 Found: C 35.97 H 4.79 N 9.28 Gd 25.83

EXAMPLE 9

(a) 6-Carboxymethyl-3-ethoxycarbonylmethyl-9-(4-methoxybenzylcarbamoylmethyl)-3,6,9-triazaundecanedioic Acid 14.10 g (35 mmol) of $N^3$-(2,6-dioxomorpholinoethyl)-$N^6$-(ethoxycarbonylmethyl)-3,6-diazaoctanedioic acid is combined in 175 ml of dimethylformamide at 0° C. with 24.4 ml (175 mmol) of triethylamine and 4.67 ml (35 mmol) of 4-methoxybenzylamine and stirred overnight at room temperature. The solvent is extensively removed by vacuum distillation and the residue is heated to boiling with 600 ml of diisopropyl ether. After cooling to room temperature, the mixture is decanted off from the solvent. The residue is dissolved in 185 ml of water and passed over a column with 140 ml of cation exchanger "IR 120" (H+ form), and the column is washed with 200 ml of water. The combined eluates are concentrated to one-third under vacuum and then freeze-dried, yielding 16.33 g of the title compound as a white powder which still contains 1.2% water and 1% dimethylformamide.

Analysis (after correction of solvent proportions): Calculated: C 53.33 H 6.71 N 10.36 Found: C 53.51 H 6.78 N 10.18

(b) 3,6-Bis(carboxymethyl)-9-(4-methoxybenzylcarbamoylmethyl)-3,6,9-triazaundecanedioic Acid 12.34 g (22 mmol) of the ethyl ester described in Example 9(a) is dissolved in 200 ml of water and 20 ml of 11N sodium hydroxide solution and stirred for 2 hours at room temperature. A pH of 2.3 is reached by addition of 140 ml of "Amberlite" IR 120 (H+ form). The mixture is filtered and the solution subjected to freeze-drying.

Yield: 9.61 g (85% of theory), water content 2.18%. Analysis (after correction of water content): Calculated: C 51.56 H 6.29 N 10.93 Found: C 51.37 H 6.44 N 10.89

(c) Gadolinium Complex of 3,6-Bis(carboxymethyl)-9-(4-methoxybenzylcarbamoylmethyl)-3,6,9-triazaundecanedioic Acid 5.24 g (10 mmol) of the complexing acid obtained according to Example 9(b) is stirred in 200 ml of water with 1.81 g (5 mmol) of gadolinium oxide for one hour at 80° C., producing an almost clear solution. The latter is filtered and the filtrate subjected to freeze-drying.

Yield: 6.31 g, water content 3.7%. Analysis (after correction of water content): Calculated: C 39.63 H 4.38 N 8.40 Gd 23.99 Found: C 39.88 H 4.53 N 8.51 Gd 23.70

(d) N-Methylglucamine Salt of the Gadolinium Complex of 3,6-Bis(carboxymethyl)-9-(4-methoxybenzylcarbamoylmethyl)-3,6,9-triazaundecanedioic Acid 2 g of the gadolinium complex obtained according to Example 9(c) is dissolved in 30 ml of water, combined with 1 equivalent of N-methylglucamine, and the solution is concentrated by evaporation under vacuum.

Yield: 2.30 g, water content 4%. Analysis (after correction of water content): Calculated: C 40.41 H 5.38 N 8.12 Gd 18.24 Found: C 40.52 H 5.11 N 8.27 Gd 18.39

(e) Sodium Salt of the Gadolinium Complex of 3,6-Bis(carboxymethyl)-9-(4-methoxybenzylcarbamoylmethyl)-3,6,9-triazaundecanedioic Acid 0.5 g of the gadolinium complex obtained in accordance with Example 9(c) is dissolved in 10 ml of water, combined with 1 equivalent of sodium hydroxide dissolved in 5 ml of water, and the solution of the title compound is subjected to freeze-drying, producing 0.55 g of the title compound as a white powder with a water content of 4.5%.

Analysis (after correction of water content): Calculated: C 38.37 H 4.10 Gd 22.83 N 8.13 Na 3.34 Found: C 38.40 H 4.45 Gd 22.43 N 8.10 Na 3.57

EXAMPLE 10

(a) 6-Carboxymethyl-3-ethoxycarbonylmethyl-9-(N-undecylcarbamoylmethyl)-3,6,9-triazaundecanedioic Acid Under a nitrogen atmosphere, 12.10 g (30 mmol) of $N^3$-(2,6-dioxomorpholinoethyl)-$N^6$-(ethoxycarbonylmethyl)-3,6-diazaoctanedioic acid in 1 liter of absolute dimethylformamide is combined at 0° C. with 12.6 ml (91 mmol) of triethylamine and 5.14 g (30 mmol) of 1-undecylamine and stirred for 16 hours at 20°–25° C. After the reaction is completed, the solvent is evaporated under vacuum and the remaining oily residue is stirred with 1 liter of diethyl ether. The thus-separated white powder is suctioned off, rinsed with 1 liter of diethyl ether in portions, and the product is dried at 40° C. under vacuum.

Yield: 14.31 g (83%), white powder. Water content: 1.41% Dimethylformamide content: 0.8% Analysis (after correction of solvent proportions): Calculated: C 56.43 H8.77 N 9.75 Found: C 56.25 H8.89 N 9.48

(b) 3,6-Bis(carboxymethyl)-9-(N-undecylcarbamoylmethyl)-3,6,9-triazaundecanedioic Acid 10 g (17.4 mmol) of the ethyl ester described in Example 10(a) is dissolved in 200 ml of 2N sodium hydroxide solution and stirred for 2 hours at room temperature. After the reaction is finished, the mixture is cooled to 5° C. and concentrated hydrochloric acid is added until a pH value of 2.15 has been attained. The thus-separated white powder is suctioned off and washed five times with 50 ml of ice water, five times with diethyl ether/ethanol (8:2), five times with 50 ml of diethyl ether, and five times with 50 ml of n-pentane.

Yield: 8.25 g (86.7%), white powder. Water content: 2.12% Dimethylformamide content: <0.05% Analysis (after correction of water content): Calculated: C 54.93 H 8.48 N 10.25 Found: C 54.78 H 8.67 N 9.98

(c) Gadolinium Complex of 3,6-Bis(carboxymethyl)-9-(N-undecylcarbamoylmethyl)-3,6,9-triazaundecanedioic Acid At 80° C., 5.47 g (10 mmol) of the complex-forming acid obtained according to Example 10(b) is stirred in 500 ml of water with 1.81 g (5 mmol) of gadolinium oxide for 4 hours, thus producing an almost clear solution. The latter is filtered and the filtrate subjected to freeze-drying.

Yield: 6.35 g (90.6%), white powder. Water content: 4.2% Analysis (after correction of water content): Calculated: C 42.84 H 6.18 N 7.99 Gd 22.44 Found: C 42.91 H 6.25 N 7.87 Gd 22.40

(d) Mono-N-methylglucamine Salt of the Gadolinium Complex of 3,6-Bis(carboxymethyl)-9-(N-undecylcarbamoylmethyl)-3,6,9-triazaundecanedioic Acid 2 g of the gadolinium complex obtained in accordance with Example 10(c) is dissolved in 35 ml of water, combined with one equivalent of N-methylglucamine, filtered, and the solution is evaporated under vacuum.

Yield: 2.25 g (88%), white powder. Water content: 3.75% Analysis (after correction of water content): Calculated: C 42.89 H 6.75 N 7.82 Gd 17.55 Found: C 42.73 H 6.89 N 7.69 Gd 17.48

EXAMPLE 11

(a) 6-Carboxymethyl-3-ethoxycarbonylmethyl-9-(1-hexadecylcarbamoylmethyl)-3,6,9-triazaundecanedioic Acid 28.20 g (70 mmol) of $N^3$-(2,6-dioxomorpholinoethyl)-$N^6$-(ethoxycarbonylmethyl)-3,6-diazaoctanedioic acid is combined in 320 ml of dimethylformamide at 0° C. with 28.8 ml (350 mmol) of triethylamine and 16.90 g (70 mmol) of 1-hexadecylamine and then stirred for 24 hours at 20°–25° C. The mixture is thereafter concentrated under vacuum and the residue stirred under boiling heat with 1 liter of methyl tert-butyl ether. After cooling to +10° C., the mixture is suctioned off, the residue dried at 45° C. under vacuum, taken up in 400 ml of water, and the solution is passed over a column with 300 ml of ion exchanger "IR 120" ($H^+$ form), the column is washed with 0.5 liter of water, and the combined eluates are concentrated under vacuum to about 300 ml, and the title compound is isolated by freeze-drying, thus obtaining 36.5 g as a white powder.

Water content: 1.70% Dimethylformamide content: 0.7% Analysis (after correction of solvent proportions): Calculated: C 59.60 H 9.38 N 8.69 Found: C 59.42 H 9.49 N 8.85

(b) 3,6-Bis(carboxymethyl)-9-(1-hexadecylcarbamoylmethyl)-3,6,9-triazaundecanedioic Acid 6.45 g (10 mmol) of the ethyl ester disclosed in Example 11(a) is dissolved in 100 ml of water and 9.1 ml of 11N sodium hydroxide solution and left for 2 hours at room temperature. Under agitation, the mixture is combined with 65 ml of ion exchanger "Amberlite" IR 120 ($H^+$ form), thus setting a pH of 2.5. The mixture is filtered and the solution is subjected to freeze-drying, thus obtaining 5.30 g of the title compound as a white powder.

Water content: 3.2% Dimethylformamide content: <0.05% Analysis (after correction of water content): Calculated: C 58.42 H 9.15 N 9.08 Found: C 58.59 H 9.44 N 8.95

(c) Monomeglumine Salt of the Gadolinium Complex of 3,6-Bis(carboxymethyl)-9-(1-hexadecylcarbamoylmethyl)-3,6,9-triazaundecanedioic Acid At 80°–85° C., 4.93 g (8 mmol) of the complex-forming acid obtained according to Example 11(b) is stirred in 170 ml of water for 2 hours with 1.45 g (4 mmol) of gadolinium oxide and 1.56 g (8 mmol) of N-methylglucamine. The almost clear solution is filtered and freeze-dried.

Yield: 7.49 g of a white powder. Water content: 2.8% Analysis (after correction of water content): Calculated: C 45.99 H 7.30 N 7.25 Gd 16.27 Found: C 46.21 H 7.55 N 7.08 Gd 16.18

By the same route as described in Example 11, the monomeglumine salt of the europium complex of 3,6-bis(carboxymethyl)-9-(1-hexadecylcarbamoylmethyl)-3,6,9-triazaundecanedioic acid can be prepared as well.

EXAMPLE 12

Preparation of a Solution of the Meglumine Salt of the Gadolinium Complex of 3,6,9-Tris(carboxymethyl)-3,6,9-triazaundecanedioic Acid Undecyl Monoamide 448.57 g (0.5 mol) of the compound described in Example 10 (d) is dissolved under heating in 600 ml of water pro injectione (p.i.). After addition of 4.92 g (10 mmol) of the monohydrate of the calciumtrisodium salt of DTPA, $CaNa_3DTPA$, the solution is filled up with water p.i. to 1000 ml. The solution is subjected to ultrafiltration, dispensed into bottles, and heat-sterilized, and is ready for use for parenteral administration.

EXAMPLE 13

Production of a Powder Form of Administration 89.61 g (0.1 mol) of the meglumine salt disclosed in Example 10(d) is finely ground up with 25 g of sucrose and 5 g of "Pluronic" F 68 and 10 mg of raspberry flavoring. The powder is filled into bags and is ready for oral administration.

EXAMPLE 14 a) 3,6-Bis(carboxymethyl)-4-benzyl-9-(undecylaminocarbonylmethyl)-3,6,9-triazaundecanedioic acid and 6,9-bis(carboxymethyl)-4-benzyl-3-(undecylaminocarbonylmethyl)-3,6,9-triazaundecanedioic acid 48.3 g (100 mmol) of 3,6,9-tris(carboxymethyl)-4-benzyl-3,6,9-triazaundecanedioic acid, produced according to EP 0 405 704, is suspended in 75 ml of acetic anhydride. 40 ml of pyridine is added and it is heated for 3 hours to 50° C. After stirring overnight, it is evaporated to dryness in a vacuum, codistilled several times with 200 ml each of toluene, again evaporated to dryness in a vacuum and the residue is mixed for partial saponification of the formed bisanhydride with 250 ml of dimethylformamide and 18 ml (100 mmol) of water. The solution is heated for three hours to 70° C., cooled to 0° C. and 72 ml (520 mmol) of triethylamine and 17.1 g (100 mmol) of undecylamine are added. After stirring overnight at room temperature, the solution is evaporated to dryness in a vacuum. The residue is dissolved in methanol and chromatographed on a silica gel column (ammonia/methanol gradient). The solution of pentaammonium salt is evaporated to dryness in a vacuum, the residue is dissolved in 500 ml of water, the solution is clarified on activated carbon and brought to pH 1.5 with concentrated hydrochloric acid. After 24 hours stirring in an ice bath, the precipitate is suctioned off, washed with water and dried in a vacuum at 50° C. 32.5 g (51% of theory) of the title compound is obtained as white powder with an uncharacteristic decomposition point.

b) Gadolinium complex of 3,6-bis(carboxymethyl)-4-benzyl-9-(undecylaminocarbonylmethyl)-3,6,9-triazaundecanedioic acid and 6,9-bis(carboxymethyl)-4-benzyl-3-(undecylaminocarbonylmethyl)-3,6,9-triazaundecanedioic acid 8.6 g (15 mmol) of the compound obtained under a) is reacted in 200 ml of water with 2.72 g (7.5 mmol) of gadolinium oxide, $Gd_2O_3$, at 90° C. for one hour. The solution is poured on a membrane filter and freeze-dried. The title compound is obtained in quantitative yield as a white powder with an uncharacteristic decomposition point.

EXAMPLE 15

3,6-Bis(carboxymethyl)-4-benzyl-9-(benzylaminocarbonylmethyl)-3,6,9-triazaundecanedioic acid and 6,9-bis(carboxymethyl)-4-benzyl-3-(benzylaminocarbonylmethyl)-3,6,9-triazaundecanedioic acid 48.3 g (100 mmol) of 3,6,9-tris(carboxymethyl)-4-benzyl-3,6,9-triazaundecanedioic acid, produced according to EP 0 405 704, is suspended in 75 ml of acetic anhydride. 40 ml of pyridine is added and it is heated for three hours to 50° C. After stirring overnight, it is evaporated to dryness in a vacuum, codistilled several times with 200 ml of toluene each, again evaporated to dryness in a vacuum and the residue is mixed for partial saponification of the formed bisanhydrides with 250 ml of dimethylformamide and 18 ml (100 mmol of water. The solution is heated for three hours to 70° C., cooled to 0° C. and 72 ml (520 mmol) of triethylamine and 10.7 g (100 mmol) of benzylamine are added. After stirring overnight at room temperature, the solution is evaporated to dryness in a vacuum. The residue is dissolved in methanol and chromatographed on a silica gel column (ammonia/methanol gradient). The solution of pentaammonium salt is evaporated to dryness in a vacuum, the residue is dissolved in 500 ml of water, the solution is clarified on activated carbon and brought to pH 1.5 with concentrated hydrochloric acid. After 24 hours stirring in an ice bath, the precipitate is suctioned off, washed with water and dried in a vacuum at 50° C. 30 g (53% of theory) of the title compound is obtained as white powder with an uncharacteristic decomposition point.

b) Gadolinium complex of 3,6-bis(carboxymethyl)-4-benzyl-9-(benzylaminocarbonylmethyl)-3,6,9-triazaundecanedioic acid and 6,9-bis(carboxymethyl)-4-benzyl-3-(benzylaminocarbonylmethyl)-3,6,9-triazaundecanedioic acid 8.6 g (15 mmol) of the compound obtained under a) is reacted in 200 ml of water with 2.72 (7.5 mmol) of gadolinium oxide, $Gd_2O_3$, at 90° C. for one hour. The solution is poured on a membrane filter and freeze-dried. The title compound is obtained in quantitative yield as white powder with an uncharacteristic decomposition point.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of NMR imaging, the improvement comprising imaging the renal system, gastrointestinal tract, liver, gall bladder or bile ducts of a subject and administering to the subject to be imaged, a diagnostically effective amount of a contrast agent wherein said agent comprises a compound of the formula

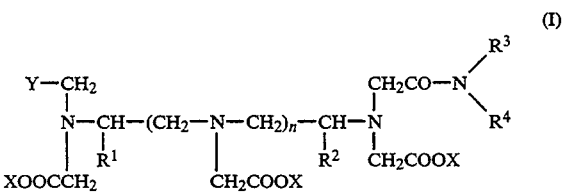

wherein n is 1;

$R^1$ and $R^2$ are each H;

$R^3$ is a saturated or unsaturated, straight-chain, branched-chain or cyclic hydrocarbon residue of up to 16 carbon atoms and at least one $R^3$ is a cycloalkyl group, or an aryl or aralkyl group optionally substituted by one or several di-$C_{1-6}$-alkylamino groups or by one or several $C_{1-6}$-alkoxy groups, $R^4$ is a hydrogen atom;

X is in each case H or a metal ion equivalent of at least one element of atomic numbers 21–29, 42, 44 or 58–70, with the proviso that at least two of the X groups represent a metal ion equivalent; and Y is a COOX— or

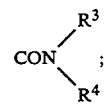

or physiologically acceptable salt thereof with an organic and/or inorganic base.

2. A method according to claim 1, wherein Y is COOX—.

3. A method according to claim 1, wherein Y is

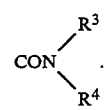

$$CON\begin{matrix}R^3\\ \diagup\\ \diagdown\\ R^4\end{matrix}.$$

4. A method according to claim 1, wherein at least one $R^3$ is $C_{3-16}$-cycloalkyl, $C_{6-10}$-aryl, $C_{6-10}$-aryl-$C_{1-6}$-alkyl, or $C_{6-10}$-aryl or $C_{6-10}$-aryl-$C_{1-6}$-alkyl substituted by one or more di-$C_{1-6}$-alkylamino or one or more $C_{1-6}$-alkoxy.

5. A method according to claim 1, wherein said compound is:
   (a) gadolinium complex of 3,6,9-tris(carboxymethyl)-3,6,9-triazaundecanedioic acid phenyl monoamide;
   (b) gadolinium complex of 3,6,9-tris(carboxymethyl)-3,6,9-triazaundecanedioic acid (N,N'-diphenyl)-diamide;
   (c) gadolinium complex of 3,6,9-tris(carboxymethyl)-3,6,9-triazaundecanedioic acid (N,N'-dibenzyl)-diamide;
   (d) gadolinium complex of 3,6,9-tris(carboxymethyl)-3,6,9-triazaundecanedioic acid benzyl monoamide;
   (e) dysprosium(III) complex of 3,6,9-tris(carboxymethyl)-3,6,9-triazaundecanedioic acid benzyl monoamide;
   (f) gadolinium complex of 3,6,9-bis(carboxymethyl)-9-(4-methoxybenzylcarbamoylmethyl)-3,6,9-triazaundecanedioic acid; or a physiologically acceptable salt of any one of (a)–(f) with organic and/or inorganic base.

6. A method according to claim 1, wherein said agent further comprises a pharmaceutically acceptable carrier.

7. A method according to claim 1, wherein said agent is sterile.

8. A method according to claim 1, wherein said agent further comprises an additional separate complexing agent.

9. A method according to claim 1, wherein said agent further comprises a physiologically acceptable buffer, an electrolyte, and/or an antioxidant.

10. A method according to claim 1, wherein said agent is administered orally.

11. A method according to claim 10, wherein said complex is administered at a concentration of 0.1 mmol/l–100 mmol/l.

12. A method according to claim 1, wherein said agent is administered intravenously.

13. A method according to claim 12, wherein said complex is administered at a concentration of 50 μmol/l–2 mol/l.

14. A method according to claim 1, wherein said complex is administered at a dosage of 1 μmol–5 mmol per kg of body weight.

15. A method according to claim 1, wherein said agent is administered to a human.

16. A method according to claim 1, wherein the renal system is imaged.

17. A method according to claim 1, wherein the liver is imaged.

18. A method according to claim 1, wherein the gall bladder is imaged.

19. A method according to claim 1, wherein bile duct(s) are imaged.

20. A method according to claim 1, wherein stomach ulcer(s) are imaged.

21. A method according to claim 1, wherein stomach carcinoma(s) are imaged.

22. A method according to claim 1, wherein said compound is the gadolinium complex of 3,6,9-tris(carboxymethyl)-3,6,9-triazaundecanedioic acid benzyl monoamide or a physiologically acceptable salt thereof with an organic and/or inorganic base.

23. A method according to claim 1, wherein at least one $R^3$ is phenyl or benzyl.

24. A method according to claim 1, wherein the pancreas of the subject is imaged.

25. In a method of NMR imaging, the improvement comprises administering to a patient with renal insufficiency a diagnostically effective amount of a contrast agent wherein said agent comprises a physiologically compatible complex compound of the formula $$\begin{matrix} Y-CH_2 & & & & CH_2CO-N\diagup R^3\\ | & & & & | & \diagdown R^4\\ N-CH-(CH_2-N-CH_2)_n-CH-N & \\ | & | & | & |\\ XOOCCH_2 & R^1 & CH_2COOX & R^2 & CH_2COOX \end{matrix} \quad (I)$$

wherein
n is 1;
$R^1$ and $R^2$ are each H;
$R^3$ is a saturated or unsaturated, straight-chain, branched-chain or cyclic hydrocarbon residue of up to 16 carbon atoms and at least one $R^3$ is a cycloalkyl group, or an aryl or aralkyl group optionally substituted by one or several di-$C_{1-6}$-alkylamino groups or by one or several $C_{1-6}$-alkoxy groups,
$R^4$ is a hydrogen atom;
X is in each case H or a metal ion equivalent of at least one element of atomic numbers 21–29, 42, 44 or 58–70, with the proviso that at least two of the X groups represent a metal ion equivalent; or
Y is a COOX— or $$CON\begin{matrix}R^3\\ \diagup\\ \diagdown\\ R^4\end{matrix};$$

or
physiologically acceptable salt thereof with an organic and/or inorganic base.

26. In a method of NMR imaging, the improvement comprises administering to a patient with a gastrointestinal disorder a diagnostically effective amount of a contrast agent wherein said agent comprises a physiologically compatible complex compound of the formula $$\begin{matrix} Y-CH_2 & & & & CH_2CO-N\diagup R^3\\ | & & & & | & \diagdown R^4\\ N-CH-(CH_2-N-CH_2)_n-CH-N & \\ | & | & | & |\\ XOOCCH_2 & R^1 & CH_2COOX & R^2 & CH_2COOX \end{matrix} \quad (I)$$

wherein
n is 1;

$R^1$ and $R^2$ are each H;

$R^3$ is a saturated or unsaturated, straight-chain, branched-chain or cyclic hydrocarbon residue of up to 16 carbon atoms and at least one $R^3$ is a cycloalkyl group, or an aryl or aralkyl group optionally substituted by one or several di-$C_{1-6}$-alkylamino groups or by one or several $C_{1-6}$-alkoxy groups, $R^4$ is a hydrogen atom;

X is in each case H or a metal ion equivalent of at least one element of atomic numbers 21–29, 42, 44 or 58–70, with the proviso that at least two of the X groups represent a metal ion equivalent;

Y is a COOX— or

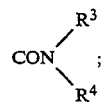

or physiologically acceptable salt thereof with an organic and/or inorganic base.

27. A method according to claim 26, wherein n is 1;

$R^1$ and $R^2$ are each H;

$R^3$ is a saturated, unsaturated, straight-chain or branched-chain or cyclic hydrocarbon residue of up to 16 carbon atoms and at least one $R^3$ is a cycloalkyl group, or an aryl or aralkyl group optionally substituted by one or several di-$C_{1-6}$-alkylamino groups or by one or several $C_{1-6}$-alkoxy groups, and $R^4$ is a hydrogen atom.

* * * * *